United States Patent [19]

Ikeya et al.

[11] Patent Number: 5,484,595
[45] Date of Patent: Jan. 16, 1996

[54] PROCESS FOR PREPARATION OF DIBENZOCYCLOOCTADIENE TYPE LIGNAN

[75] Inventors: Yukinobu Ikeya; Hirotoshi Kanatani; Kaoru Nakajima; Hiroshi Mitsuhashi, all of Ibaraki, Japan

[73] Assignee: Tsumura & Co., Tokyo, Japan

[21] Appl. No.: 477,875

[22] PCT Filed: Aug. 8, 1989

[86] PCT No.: PCT/JP89/00809

§ 371 Date: Apr. 6, 1990

§ 102(e) Date: Apr. 6, 1990

[87] PCT Pub. No.: WO90/01487

PCT Pub. Date: Feb. 22, 1990

[30] Foreign Application Priority Data

Aug. 9, 1988 [JP] Japan .................................. 63-197242

[51] Int. Cl.⁶ .......................... A61K 35/78; A61K 31/70; A23L 1/28
[52] U.S. Cl. .......................... 424/195.1; 426/655; 514/22
[58] Field of Search .................. 424/195.1; 426/655; 514/22

[56] References Cited

U.S. PATENT DOCUMENTS

| | | | |
|---|---|---|---|
| 4,059,593 | 11/1977 | Kende | 260/340.5 R |
| 4,340,676 | 7/1982 | Bourque | 435/232 |
| 4,684,628 | 8/1987 | Liu | 514/26 |
| 4,981,688 | 1/1991 | Ayroles | 424/195.1 |
| 4,990,647 | 2/1991 | Himmler | 558/414 |
| 4,996,331 | 2/1991 | Kimura | 549/229 |
| 5,032,685 | 7/1991 | Matsuoka | 549/436 |

FOREIGN PATENT DOCUMENTS

| | | | |
|---|---|---|---|
| 55-22612 | 2/1980 | Japan . | |
| 189221 | 8/1986 | Japan . | |
| 61-189221 | 8/1986 | Japan . | |
| 61-282315 | 12/1986 | Japan . | |
| 282315 | 12/1986 | Japan | 424/195.1 |
| 63-119422 | 5/1988 | Japan . | |

OTHER PUBLICATIONS

Kirk–Othmer Encyclopedia of Chem Technology 3rd ed vol. 9 John Wiley N.Y. 1979 pp. 672–676.
Ikeya, Y. Chem Pharm Bull vol. 30(9) 1982 Constituents of SC XI pp. 3202–3206.
Ikeya Y. Chem Pharm Bull vol. 30(9) 1982 Constituents of SC XII pp. 3207–3211.
Chemical Research of Natural Material 1982.
Li, L. Planta Medica 1986 Further Dibenzocyclo . . . vol. 5 p. 460.
Ikeya, Y. Phytochemistry vol. 27 No. 2 pp. 569–573 A Lignan From *S. chinensis* 1988.
Ikeya Y. Chem Pharm Bull, Constituents of SC XV. 36 (10) 3974–3979. 1988.
Li, L. Three New Dibenzocyclooctadiene Lignans Planta Med 57 (1991) pp. 169–171.
Ikeya Y. Benzoylgomisin Q . . . Chem. Pharm Bull 38(5) 1408–1411.
"Natural Materials for Medicines" Aug. 1982 Trans. Nanzandoh Publishing Co., pp. 101 to 105.

*Primary Examiner*—Michael G. Wityshyn
*Assistant Examiner*—Ralph G. Gitomer
*Attorney, Agent, or Firm*—Burns, Doane, Swecker & Mathis

[57] ABSTRACT

A dibenzocyclooctadiene type lignan can be efficiently prepared by extracting a plant containing a dibenzocyclooctadiene type lignan with a low polar solvent, subjecting the resulting extract to partition extraction with a water-insoluble low polar solvent and a water-soluble high polar solvent, at least one time, and recovering the dibenzocyclooctadiene type lignan from the layer of the water-soluble high polar solvent.

10 Claims, No Drawings

PROCESS FOR PREPARATION OF DIBENZOCYCLOOCTADIENE TYPE LIGNAN

DESCRIPTION

1. Technical Field

The present invention relates to a process for the preparation of dibenzocyclooctadiene type lignan which is valuable as a medicine.

2. Background Art

It is generally known that many dibenzocyclooctadiene type lignans are effective as medicines. For example, it is known that schizandrin comprises analgesic action, gomisin A and gomisin C comprise liver trouble-moderating action, and deoxyschizandrin exhibits anti-ulcer action.

It is known in the art to obtain dibenzocyclooctadiene type lignans from plants to treat plant extracts containing said lignans to chromatography using as the adsorbent, for example, silica gel, ODS silica gel, alumina, Celite or a porous polymer gel such as Dia-Ion HP-20 repeatedly to effect purification. But the process comprising subjecting a plant extract containing large quantities of impurities directly to the chromatography is defective as an industrial preparation process because a large quantity of the adsorbent must be used, the deterioration speed of the adsorbent is high, and a large quantity of the solvent must be used for the chromatography. To use a specific dibenzocyclooctadiene type lignan as a medicine, it is necessary to prepare this lignan in a large quantity, and therefore, a simple process capable of providing an intended lignan in a large quantity is desired.

Disclosure of the Invention

The inventors carried out research with a view to developing a process capable of providing a large quantity of a dibenzocyclooctadiene type lignan by simple means, and as a result, found that, if the partition extraction method is adopted, the amounts of the adsorbent and solvent used for the chromatography can be greatly reduced and an intended dibenzocyclooctadiene type lignan can be very simply prepared in a large quantity. The present invention is based on this finding.

More specifically, in accordance with the present invention, there is provided a process for the preparation of a dibenzocyclooctadiene type lignan, which comprises extracting a plant containing a dibenzocyclooctadiene type lignan with a low polar solvent, subjecting the resulting extract to the partition extraction using a water-insoluble low polar solvent and a water-soluble high polar solvent at least one time, and recovering the dibenzocyclooctadiene type lignan from the layer of the water-soluble high polar solvent.

Best Mode of Carrying Out the Invention

As the dibenzocyclooctadiene type lignan-containing plant to be extracted in the present invention, there can be mentioned plants belonging to the family Schisandraceae, such as *Schisandra chinensis* Baill., *Schisandra sphenathera* Rehd. et Wils., *Schisandra rubriflola* and *Kadsura japonica*.

As specific examples of the low polar solvent valuably used in the present invention, there can be mentioned petroleum ether, n-hexane, n-heptane, benzene, toluene and cyclohexane. The extraction is carried out at a temperature in the range of from room temperature to the boiling point of the used solvent, preferably under heating.

Then, the extract is subjected to the partition extraction (hereinafter referred to as "partition") using a water-insoluble low polar solvent and a water-soluble high polar solvent. If the solvent used for the partition is the same as the solvent used for the extraction, then preferably the partition is carried out after the extract has been condensed at an appropriate concentration or dried. If the solvent used for the partition is different from the solvent used for the extraction, preferably the partition is carried out after the extract has been dried.

As specific examples of the low-polarity water-insoluble solvent, there can be mentioned petroleum ether, n-hexane, n-heptane, benzene, toluene and cyclohexane, and as the high-polarity water-soluble solvent, there can be mentioned methanol and ethanol. The proportion of the high-polarity water-soluble solvent in the solvent is preferably from 40 to 80%, most preferably from 55 to 65%. The partition can be performed by customary procedures.

The partition can be accomplished more efficiently if a salt is added. As the salt sodium chloride, potassium chloride, ammonium sulfate and sodium sulfate can be used. When a salt is added, a partition with chloroform or the like is preferably carried out, to remove the salt from the high-polarity water-soluble solvent.

After the above-mentioned partition operation, to obtain the intended dibenzocyclooctadiene type lignan from the high-polarity water-soluble solvent layer, such means as concentration, drying, filtration, recrystallization, column chromatography, and high-speed liquid chromatography can be adopted. Recrystallization can be carried out according to customary procedures by using a solvent selected from water, petroleum ether, n-hexane, n-heptane, benzene, toluene, cyclohexane, chloroform, methylene chloride, ether, tetrahydrofuran, ethyl acetate, acetone, ethanol, methanol and isopropanol, or two or more mixed solvent of above solvents. When column chromatography is carried out by using an adsorbent such as silica gel, ODS silica gel, alumina or a porous polymer gel, single or mixed solvent selected from petroleum ether, n-hexane, benzene, toluene, chloroform, methylene chloride, ether, ethyl acetate, acetone, ethanol, methanol and water can be used as the solvent.

When high-speed liquid chromatography is carried out, a commercially available column of the normal phase or reversed phase can be used, and an organic solvent suitable for the column used can be used as the moving phase.

The foregoing operations can be carried out in combination, according to need.

As specific examples of the dibenzocyclooctadiene type lignan obtained according to the above-mentioned procedures, gomisin A, schizandrin, deoxyschizandrin and gomisin C can be mentioned.

The present invention will now be described in detail with reference to the following examples, that by no means limit the scope of the invention.

EXAMPLE 1

*Schisandra chinensis* Baill. (10 kg) was refluxed and extracted for 1.5 hours with 50 l of hexane, the extract was dried under a reduced pressure to obtain 978.8 g of a hexane extract, the hexane extract dissolved in 9.8 l of hexane, and then extracted two times with 9.8 l of 60% (v/v) methanol.

Two extracts (lower layers) were combined, and the mixture was dried under a reduced pressure to obtain 112.2 g of a fraction having a high lignan content.

The above-mentioned fraction having a high lignan content was subjected to the fractionation high-speed liquid chromatography [column: Kiesel Gel 60 (230 to 400 mesh) supplied by Merk, diameter=10 cm, length= 100 cm, moving phase: n-hexane/ethyl acetate (7/3), flow rate: 200 ml/min, apparatus: Waters Prep LC/System 500A]. Fractions eluted at 123 to 133 minutes were combined and dried under a reduced pressure, and the residue was recrystallized from methanol to obtain 11.66 g of a colorless needle crystal. The physical and chemical properties of this colorless needle crystal were in agreement with those of gomisin A described in the literature reference [H. Taguchi and Y. Ikeya, Chem. Pharm. Bull., 23(12), 3296 (1975)].

EXAMPLE 2

Fractions eluted at 140 to 170 minutes in the fractionation high-speed liquid chromatography conducted in Example 1 were combined and dried under a reduced pressure. The obtained residue was recrystallized from a mixed solvent of ether and n-hexane to obtain 950 mg of a colorless prism crystal. The physical and chemical properties of this colorless prism crystal were in agreement with those of Schizandrin disclosed in the literature reference [Y. Ikeya, H. Taguchi, I. Yoshioka and H. Kobayashi, Chem. Pharm. Bull., 27(6), 1383(1979)].

EXAMPLE 3

Fractions eluted at 63 to 70 minutes in the fractionation high-speed liquid chromatography conducted in Example 1 were combined and dried under a reduced pressure, and the obtained residue was recrystallized from methanol to obtain 1.05 g of a colorless prism crystal. The physical and chemical properties of the obtained colorless prism crystal were in agreement with those of deoxyschizandrin disclosed in the literature reference [N. K. Kochetkov, A. Khorlin and O. S. Chizov, Tetrahedron Letters, 1962, 361].

EXAMPLE 4

*Schisandra chinensis* Baill. (1 kg) was refluxed and extracted for 2 hours with 5 l of hexane, and the extract was dried and 99.5 g of the obtained hexane extract was dissolved in 1 l of n-hexane and extracted two times with 1 l of 50% (v/v) of methanol. The two extracts (lower layers) were combined and lignans were extracted with chloroform, the chloroform extract was washed with water and dried under a reduced pressure, and 12.40 g of the obtained residue was subjected to the column chromatography using 200 g of silica gel (Kiesel Gel 60 supplied by Merk, 70 to 230 mesh). After elution with 1 l of n-hexane/ethyl acetate (85/15), elution was carried out with 2 l of n-hexane/ethyl acetate (3/1). Fractions eluted with n-hexane/ethyl acetate (3/1) were combined and dried under a reduced pressure, and the residue was recrystallized from methanol to obtain 669 mg of gomisin A in the form of a colorless needle crystal.

EXAMPLE 5

In 1 l of n-hexane 99.5 g of the n-hexane extract obtained in Example 4 was dissolved, and the solution was extracted with 1 l of sodium chloride-saturated 60% (v/v) methanol two times. The two extracts (lower layers) were combined, and lignans were extracted with 1 l of chloroform. The chloroform extract was washed with water and dried under a reduced pressure, and 12.61 g of the obtained residue was recrystallized from methanol to obtain 483 mg of Gomisin A in the form of a colorless needless crystal.

EXAMPLE 6

The chloroform extract (12.40 g) obtained in Example 4 was subjected to the column chromatography using ODS silica gel [column: YMC Gel ODS 1–25/45, diameter=3 cm, length=50 cm, moving phase: methanol/water (7/3), flow rate: 6 ml/min]. The eluate obtained at 50 to 110 minutes was dried under reduced pressure and the residue was recrystallized from ether/n-hexane to obtain 1.35 g of Schizandrin in the form of a colorless prism crystal. Furthermore, the fraction eluted at 150 to 200 minutes was dried under a reduced pressure, and the obtained residue was recrystallized from methanol to give 1.26 g of gomisin A as a colorless needle crystal.

EXAMPLE 7

In 1 l of n-hexane 99.5 g of the n-hexane extract obtained in Example 4 was dissolved, and the solution was extracted with 1 l of sodium chloride-saturated 65% (v/v) methanol two times. The two extracts (lower layers) were combined, and lignans were extracted with 1 l of chloroform. The chloroform extract was washed with water and dried under a reduced pressure, and 12.53 g of the obtained residue was recrystallized from methanol to obtain 467 mg of gomisin A as a colorless needle crystal.

EXAMPLE 8

In 1 l of n-hexane 99.5 g of the n-hexane extract obtained in Example 4 was dissolved, and the solution was extracted with 1 l of sodium chloride-saturated 70% (v/v) methanol two times. The two extracts (lower layers) were combined and lignans were extracted with 1 l of chloroform two times. The chloroform extracts were combined, washed with water and dried under a reduced pressure, and 14.01 g of the obtained residue was recrystallized from methanol to obtain 422 mg of Gomisin A as a colorless needle crystal.

EXAMPLE 9

*Schisandra chinensis* Baill. (300 g) was refluxed and extracted for 3 hours with 3 l of petroleum ether, and the extract was dried under a reduced pressure and 28.7 g of the petroleum ether extract was dissolved in 280 mg of petroleum ether. The solution was extracted with 280 ml of ammonium sulfate-containing 60% (v/v) methanol two times. The two extracts were combined and lignans were extracted with 280 ml of chloroform. The chloroform extract was washed with water and dried under a reduced pressure and 4.68 g of the obtained residue was subjected to the column chromatography using 80 g of silica gel (Kiesel Gel 60 supplied by Merk, 230 to 400 mesh). After elution with 0.6 l of n-hexane/ethyl acetate (4/1), elution was carried out with 0.3 l of n-hexane/ethyl acetate (7/3). The n-hexane/ethyl acetate (7/3) eluate was dried under reduced pressure and 967 mg of the residue was recrystallized from methanol to give 305 mg of gomisin A as a colorless needle crystal.

EXAMPLE 10

*Schisandra sphenanthera* Rehd. et Wils. (435 g) was refluxed and extracted for 3 hours with 2 l of n-hexane two times. The extract was dried under a reduced pressure to obtain 43.40 g of an n-hexane extract. The n-hexane extract was dissolved in 430 ml of n-hexane, and partition extraction was carried out with 430 ml of sodium chloride-saturated 60% (v/v) methanol two times. The two extracts (lower layers) were combined and lignans were extracted with 430 ml of chloroform. The chloroform extract was washed with water and dried under a reduced pressure to obtain 6.84 g of a fraction having a high lignan content. This fraction having a high lignan content was subjected to the column chromatography (diameter=5 cm, length=15 cm) using silica gel (Kiesel 60 supplied by Merk, 230 to 400 mesh), and elution was carried out with a mixed solvent of n-hexane and ethyl acetate. Namely, 400 ml of n-hexane/ethyl acetate (7/3), 200 ml of n-hexane/ethyl acetate (6/4) and then, 200 ml of n-hexane/ethyl acetate (1/1). The n-hexane/ethyl acetate (1/1) eluate was dried under a reduced pressure and the residue was recrystallized from methanol to give 430 mg of a colorless prism crystal. The physical and chemical properties of this colorless prism crystal were in agreement with those of gomisin C disclosed in the literature reference [H. Taguchi and Y. Ikeya, Chem. Pharm. Bull., 23(12), 3296 (1975)].

Industrial Applicability

The present invention can be advantageously utilized for the production of dibenzocyclooctadiene type lignans valuable as medicines.

We claim:

1. A process for the preparation of a dibenzocyclooctadiene type lignan, which comprises extracting a plant containing a dibenzocyclooctadiene type lignan with a low polar solvent selected from the group consisting of petroleum ether, n-hexane, n-heptane, benzene, toluene and cyclohexane, subjecting the resulting extract to at least one partition extraction with a water-insoluble low polar solvent selected from the group consisting of petroleum ether, n-hexane, n-heptane, benzene, toluene and cyclohexane, and a water-soluble high polar solvent selected from the group consisting of methanol and ethanol, and recovering the dibenzocyclooctadiene type lignan from the layer of the water-soluble high polar solvent.

2. A process according to claim 1, wherein the plant containing a dibenzocyclooctadiene type lignan is selected from the group consisting of *Schisandra chinensis* Baill., *Schisandra sphenathera* Rehd. et Wils. *Schisandra rubriflola* and *Kadsura japonica*.

3. A process according to claim 1, wherein the same low polar solvent is used during the initial extraction and the partition extraction, and the partition extraction is carried out after the extract has been condensed or dried.

4. A process according to claim 1, wherein a different polar solvent is used during the initial extraction than is used during the partition extraction, and the partition extraction is carried out after the extract has been dried.

5. A process according to claim 1, wherein the proportion of the water-soluble high polar solvent in the solvent used for the partition extraction is 40 to 80%.

6. A process according to claim 5, wherein said proportion is 55 to 65%.

7. A process according to claim 1, wherein the partition extraction is carried out in the presence of a salt.

8. A process according to claim 7, wherein the salt is selected from the group consisting of sodium chloride, potassium chloride, ammonium sulfate and sodium sulfate.

9. A process according to claim 1, wherein the dibenzocyclooctadiene type lignan is recovered by concentration, drying filtration, recrystallization, column chromatography or high-speed liquid chromatography.

10. A process according to claim 1, wherein the obtained dibenzocyclooctadiene type lignan is selected from the group consisting of gomisin A, schizandrin, deoxyshizandrin and gomisin C.

* * * * *